(12) United States Patent
Chen et al.

(10) Patent No.: US 6,660,528 B1
(45) Date of Patent: Dec. 9, 2003

(54) METHOD FOR MONITORING CONTAMINATING PARTICLES IN A CHAMBER

(75) Inventors: Horng-Wen Chen, Taichung (TW); Jeng-Fieng Lu, Hsin-chu (TW); Chiang-Jen Peng, Hsin chu (TW)

(73) Assignee: Taiwan Semiconductor Manufacturing Co., Ltd., Hsin Chu (TW)

( * ) Notice: Subject to any disclaimer, the term of this patent is extended or adjusted under 35 U.S.C. 154(b) by 0 days.

(21) Appl. No.: 09/547,431

(22) Filed: Apr. 12, 2000

(51) Int. Cl.$^7$ ............................................. G01N 21/00
(52) U.S. Cl. .................... 436/171; 436/10; 422/83; 73/861.41; 73/861.42
(58) Field of Search .................... 436/10, 171; 422/83; 73/861.41, 861.42

(56) References Cited

U.S. PATENT DOCUMENTS 5,728,602 A * 3/1998 Bellows et al. ................ 438/14
5,730,181 A * 3/1998 Doyle et al. ............. 137/487.5
6,279,503 B1 * 8/2001 Choi et al. .................. 118/715

* cited by examiner

*Primary Examiner*—Jill Warden
*Assistant Examiner*—LaToya Cross
(74) *Attorney, Agent, or Firm*—Tung & Associates

(57) ABSTRACT

A method for determining the number of contaminating particles in a process chamber is described. While the method is particularly suited for detecting particles in a metal etch chamber, the present invention novel method can be utilized in any other semiconductor process chambers as long as there is a particle contamination problem. The method is carried out by conducting at least two particle dislodging cycles each including a step of flowing at least one process gas used in the process into the chamber at a flow rate of at least 30 sccm, and then evacuating the at least one process gas from the chamber to a pressure of not higher than 1 mTorr. Typical process gas that can be utilized in a metal etch chamber includes $Cl_2$, $BCl_3$ and Ar. The process gas should be flown into the etch chamber until a chamber pressure of at least 6 mTorr is reached, and preferably until at least a chamber pressure of 8 mTorr is reached. After the particle dislodging cycles are conducted, the number of particles that have fallen onto a top surface of the substrate can be counted by a particle counter.

20 Claims, 2 Drawing Sheets

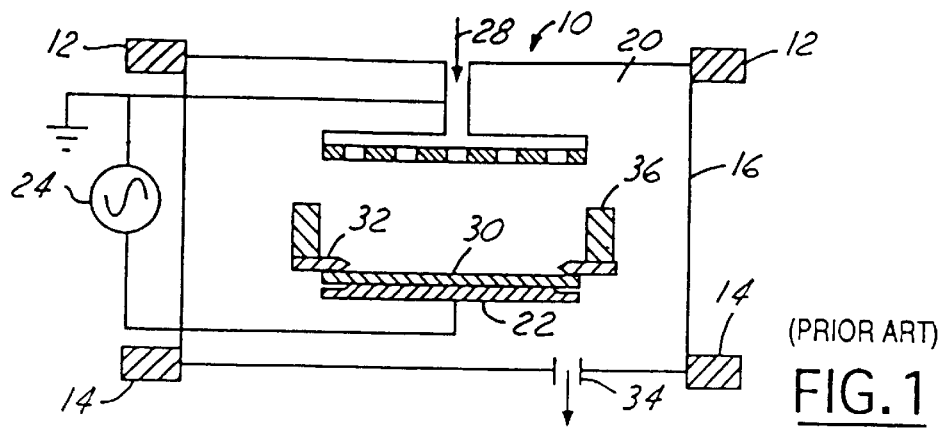
(PRIOR ART) FIG. 1
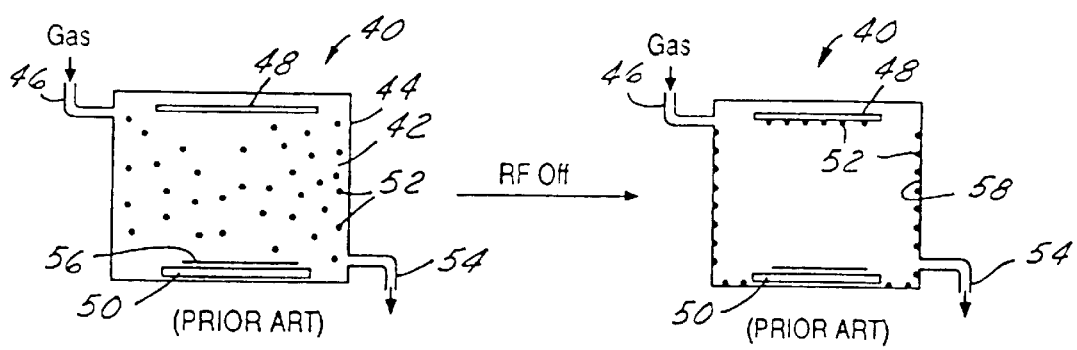
(PRIOR ART) FIG. 2A
(PRIOR ART) FIG. 2B

| Wafer ID | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| AEI- ADI | 0 | 0 | 0 | 3 | 1 | 0 | 0 | 0 | 1 | 0 | 3 | 0 | 2 | 0 | 2 | 1 | 0 | *0 | **74 | *1 | 0 | 0 | 0 | 1 |

METHOD FOR MONITORING CONTAMINATING PARTICLES IN A CHAMBER

FIELD OF THE INVENTION

The present invention generally relates to a method for operating a process chamber and more particularly, relates to a method for operating a plasma process chamber and determining the number of contaminating particles in the chamber generated by the plasma process.

BACKGROUND OF THE INVENTION

In the fabrication of semiconductor integrated circuit (IC) devices, various device features such as insulation layers, metallization layers, passivation layers, etc. are formed on a semi-conducting substrate. It is known that the quality of an IC device fabricated is a function of the processes in which these device features are formed. The yield of an IC fabrication process is in turn a function of the quality of the device fabricated and a function of the cleanliness of the manufacturing environment in which the IC device is processed.

The ever increasing trend of miniaturization of semiconductor IC devices occurring in recent years requires more stringent control of the cleanliness in the fabrication process or the processing chamber in which the process is conducted. This leads to a more stringent control of the maximum amount of impurities and contaminants that are allowed in a process chamber. When the dimension of a miniaturized device approaches the sub-half-micron level, even a minutest amount of contaminants can significantly reduce the yield of the IC manufacturing process. For instance, the yield of the process can be drastically reduced by the presence of contaminating particles during deposition or etching of films which leads to the formation of voids, dislocations or short-circuits resulting in performance and reliability problems in the IC devices fabricated.

In recent years, contamination caused by particles or films has been reduced by the improvements made in the quality of clean rooms and by the increasing utilization of automated equipment which are designed to minimize exposure to human operators. However, even though contaminants from external sources have been reduced, various contaminating particles and films are still generated inside the process chamber during the processing of semiconductor wafers. Some possible sources of contamination that have been identified include the process gases and liquids, the interior walls of the process chambers and the mechanical wear of the wafer handling equipment. The chances of generating contaminating particles are also increased in process chambers that are equipped with plasma enhancement. Various chemically reacted fragments are generated from the processing gases which include ions, electrons and radicals. These fragments can combine and form negatively charged particles which may ultimately contaminate a substrate that is being processed in the chamber. Various other materials, such as polymeric films may also be coated on the process chamber walls during plasma processing. The films may dislodge and fall from the process chamber walls when subject to mechanical and thermal stresses such that they fall onto the wafers that are being processed.

An example for illustrating chamber wall contamination in an etcher is shown in FIG. 1. Etcher 10 is a plasma etching chamber that is equipped with magnetic field enhancement generated by an upper rotating magnet 12 and a lower rotating magnet 14. The plasma etcher 10 includes a housing 16 that is typically made of a non-magnetic material such as aluminum which defines a chamber 20. A substrate holder 22 which is also a cathode is connected to a RF generator 24 and is in turn connected to a gas inlet (or showerhead) 26. The showerhead 26 also acts as an anode. A process gas 28 is supplied to chamber 20 through the gas inlet 26. A semi-conducting substrate 30 to be processed is positioned on the substrate holder or cathode 22.

The semi-conducting substrate 30 is normally held against the substrate holder 22 by a clamp ring 32. During a plasma etching process, a semi-conducting wafer 30 heats up significantly during the process and must be cooled by a cooling gas from a cooling gas supply (not shown) such that heat can be transferred to a water cooled wafer holder 36. The function of the clamp ring 32 is also to hold the substrate 30 down against the pressure generated by the cooling gas. An exhaust port 34 which is connected to a vacuum pump (not shown) evacuates the chamber. During an etching process, the upper rotating magnet 12 and the lower rotating magnet 14 function together to provide a magnetic field inside the process chamber 20.

In a conventional cleaning process for the plasma etch chamber 10, a cleaning gas supply is first flown through the gas inlet port 26 into the chamber 20 and then, the RF generator 24 is turned on. The cleaning procedure is conducted after a predetermined number, i.e. between 100–500 of wafers have been processed in chamber 20. A plasma of the cleaning gas ions is formed in the space between the showerhead 26 and the wafer holder 32 to loosen the contaminating particles and films from the chamber walls and the showerhead 26 or the upper electrode.

In etching polysilicon or metal, a chlorine etching gas is frequently used, while etching gas used for oxide or nitride is frequently a fluorine gas. During a plasma etching process, the reactive plasma ions have a high energy level and therefore can easily combine with any available chemical fragments or elements in the chamber to form contaminating particles or films. For instance, in a metal etching process, the elements frequently seen in the etch chamber includes C, H, N, O, Al, Ti, TiN and Si. Different elements such as C, N, O, Br, Si and W are seen in a polysilicon etch chamber. The contaminating particles or films formed by often volatile chemical fragments or elements during an etching process float or suspend in the chamber due to the interaction with high energy plasma ion particles when the RF power is on. The phenomenon of the floating or suspended particles can be explained by the fact that the particles have higher energy and temperature while suspended in a plasma cloud. However, at the end of a conventional etching process, the RF power is switched off which leads to the sudden loss of energy in the suspended contaminating particles and causing them to fall or stick to the chamber walls or the upper electrode. This is shown in FIGS. 2A and 2B.

FIG. 2A shows a simplified etch chamber 40 equipped with a chamber cavity 42 defined by chamber walls 44. A process gas inlet 46 is used to flow a process gas into the chamber cavity 42. An upper electrode 48 and a lower electrode/wafer holder 50 are used to supply RF power to the chamber and to produce plasma ions. A gas outlet 54 is used to evacuate the process gas from the chamber cavity 42 at the end of the etching process. During the etching process, contaminating particles 52 formed as etch byproducts are buoyant and are suspended in the chamber cavity 42. A wafer 56 is supported by the wafer holder 50 for processing.

After a conventional etching process is conducted, the RF power is turned off. The suspended, contaminating byproducts or particles 52 are easily deposited on chamber walls 58, upper electrode 48 and wafer 50. These contaminating particles (or films) are frequently formed of a carbon or chlorine containing polymeric material and when adhered to the chamber wall 58, are very difficult to remove from the chamber. Conventionally, a wet cleaning process must be conducted after approximately 2,000–3,000 wafers have been processed in the etch chamber 40. The wet cleaning process is carried out by using cleaning solvent such as IPA, deionized water, combination IPA/deionized water or the more volatile acetone. The wet cleaning process is time consuming and may be hazardous to personnel due to the toxic nature of the contaminating byproducts and the highly volatile cleaning solvent used. A wet cleaning process may cause a downtime on an etcher for as long as a whole day.

The contaminating particles or films present a serious problem in an IC fabrication process. The more contaminating particles are present, the more fabrication loss will result. It is known that a metal etching process is a heavy polymer process that readily produces contaminating particles for the chamber and induces particle spikes (a sudden surge in particle contamination). When a particle falls on a wafer, it acts as a mask during etching to cause insufficient etching and possible metal bridging. It is therefore an important task to determine the number of contaminating particles that are present in a process in a chamber in order to determine the necessity of a wet cleaning process.

In a conventional particle monitoring method, a recipe of 12 mTorr/100 sccm $Cl_2$/60 sec is used. This is shown by the solid line in FIG. 3. The method of flowing a chlorine gas at 100 sccm flow rate to reach a chamber pressure of 12 mTorr for monitoring particles in a process chamber is inadequate. The method does not reflect a true chamber condition and cannot detect a particle spike phenomenon. The constant flow of chlorine gas into the process chamber does not detach or loosen contaminating particles or films adhered to the interior chamber wall of the process chamber. The method therefore cannot be used to predict the occurrence of the particle spike phenomenon and let alone providing a solution to such problem.

It is therefore an object of the present invention to provide a method for determining the number of contaminating particles in a process chamber that does not have the drawbacks or shortcomings of the conventional methods.

It is another object of the present invention to provide a method for determining the number of contaminating particles in a process chamber by a series of gas flow/gas evacuation processes to dislodge contaminating particles from the interior chamber wall.

It is a further object of the present invention to provide a method for determining the number of contaminating particles in a process chamber by carrying out at least two cycles of a gas flow/gas evacuation process in the process chamber.

It is another further object of the present invention to provide a method for determining the number of contaminating particles present in a process chamber by repeatedly flowing and evacuating at least one process gas in and out of the process chamber.

It is still another object of the present invention to provide a method for determining the number of contaminating particles in an etch chamber by flowing into and evacuating from the etch chamber at least one etch gas used in the etch process.

It is yet another object of the present invention to provide a method for determining the number of contaminating particles in an etch chamber by flowing at least one process gas into the chamber at a flow rate of at least 30 sccm and then evacuating the gas and repeating the cycle for at least two times.

It is still another further object of the present invention to provide a method for monitoring contaminating particles in an etch chamber by flowing at least one etch gas of $Cl_2$, $BCl_3$ and Ar into the etch chamber to a chamber pressure of at least 8 mTorr, evacuating the at least one etch gas and repeating the cycle for at least two times.

It is yet another further object of the present invention to provide a method for determining the number of contaminating particles in a metal etch chamber by repeating at least three cycles of flowing a process gas into the chamber at a flow rate of at least 30 sccm and then evacuating the process gas from the chamber until a chamber pressure not higher than 1 mTorr is reached.

SUMMARY OF THE INVENTION

In accordance with the present invention, a method for determining the number of contaminating particles in a process chamber, and particularly in a metal etch chamber is provided.

In a preferred embodiment, a method for determining the number of contaminating particles in a process chamber can be carried out by the operating steps of first providing a process chamber that is equipped with a gas inlet and a plasma source, conducting a chemical process on a substrate that generates contaminating particles in the chamber, evacuating the process gas from the chamber to a pressure of not higher than 1 mTorr, flowing at least one process gas used in the chemical process into the chamber at a flow rate of at least 30 sccm, evacuating the at least one processed gas from the chamber to a pressure of not higher than 1 mTorr, flowing for the second time at least one process gas used in the chemical process into the chamber at a flow rate of at least 30 sccm, evacuating for the second time the at least one process gas from the chamber to a pressure of not higher than 1 mTorr, and counting number of particles that have fallen onto a top surface of the substrate.

In the method for determining the number of contaminating particles in a process chamber, the flowing/evacuating steps are repeated at least two times, or repeated at least three times. The method may further include the step of evacuating the process gas from the chamber by a factory vacuum system. The method may further include the step of flowing the at least one process gas used in the chemical process into the chamber to a chamber pressure of at least 6 mTorr, or to a chamber pressure of at least 8 mTorr. The method may further include the step of flowing the at least one process gas by flowing $Cl_2$ gas into the chamber to a chamber pressure of at least 8 mTorr. The method may further include the step of flowing the at least one process gas by flowing $Cl_2$ into the chamber at a flow rate not less than 80 sccm.

The method for determining the number of contaminating particles in a process chamber may further include the step of flowing the at least one process gas by flowing $BCl_3$ gas into the chamber to a chamber pressure of at least 8 mTorr. The method may further include the step of flowing at least one process gas by flowing $BCl_3$ gas into the chamber at a flow rate not less than 70 sccm. The method may further include the step of flowing the at least one process gas by flowing Ar gas into the chamber to a chamber pressure of at least 8 mTorr, or at a flow rate not less than 30 sccm. The method may further include the step of flowing the at least one process gas by flowing $Cl_2$ at a flow rate not less than 80 sccm, $BCl_3$ at a flow rate not less than 70 sccm and Ar at a flow rate not less than 30 sccm into the chamber, or flowing the $Cl_2$, $BCl_3$ and Ar gas into the chamber to a chamber pressure of at least 8 mTorr.

The present invention is further directed to a method for detecting contaminating particles in an etch chamber that has polymeric or metal based particles adhered to an interior chamber wall which can be carried out by the operating steps of first providing an etch chamber equipped with a plasma source, conducting a metal etching process in the etch chamber thus generating polymeric or metal based contaminating particles adhered to an interior chamber wall, evacuating the etch chamber to a pressure of not higher than 1 mTorr, conducting a particle dislodging cycle in the etch chamber including the steps of flowing at least one etch gas into the chamber at a flow rate of not less than 30 sccm, and evacuating the at least one etch gas from the chamber to a pressure of not higher than 1 mTorr, repeating the particle dislodging cycle at least once, and detecting the contaminating particles present on a top surface of the substrate.

The method for detecting contaminating particles in an etch chamber may further include the step of detecting the contaminating particles present on the substrate by a KLA particle counter. The method may further include the step of flowing at least one etch gas into the chamber selected from the group consisting of $Cl_2$, $BCl_3$ and Ar until a chamber pressure of 8 mTorr is reached, or flowing at least one etch gas into the chamber selected from the group consisting of $Cl_2$, $BCl_3$ and Ar at a flow rate between about 30 sccm and about 120 scm. The method may further include a step of repeating the particles dislodging cycle at least twice. The method may further include the step of flowing $Cl_2$ at a flow rate not less than 80 sccm, $BCl_3$ at a flow rate not less than 70 sccm and Ar at a flow rate not less than 30 sccm into the chamber.

BRIEF DESCRIPTION OF THE DRAWINGS

These and other objects, features and advantages of the present invention will become apparent from the following detailed description and the appended drawings in which:

FIG. 1 is an illustration of a cross-sectional view of a conventional plasma enhanced etch chamber for etching a semi-conductor substrate.

FIG. 2A is a simplified cross-sectional view of a conventional-chamber during an etch process with the RF power on and the contaminating byproducts suspended in a chamber.

FIG. 2B is a simplified cross-sectional view of the etch chamber of FIG. 2A after the RF power is switched off and the contaminating byproducts are attached to the chamber walls.

DETAILED DESCRIPTION OF THE PREFERRED EMBODIMENT

Figures 3, 4:
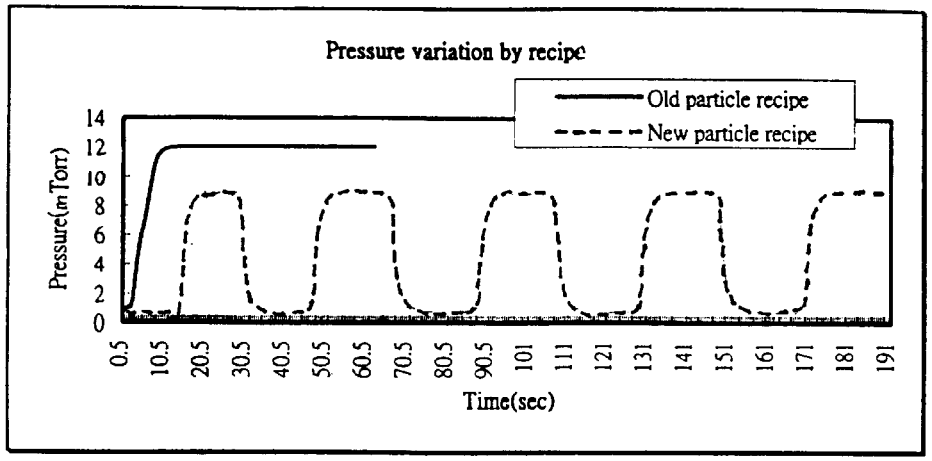
FIG. 3 is a graph illustrating the dependency of the pressure of purge gas on time for a conventional purge method and for a present invention purge method.
FIG. 4 is a chart containing data obtained on a wafer lot of 24 wafers showing particles detected after an etching process is conducted on the wafers.

The present invention discloses a method for monitoring contaminating particles in a semiconductor process chamber, and particularly in a plasma enhanced etch chamber for particles of polymeric nature produced by a sidewall passivation process.

The present invention novel method utilizes a particle dislodging cycle which consists of a first step of flowing a process gas into the plasma chamber at a flow rate of at least 30 sccm, followed by a second step of evacuating the process gas from the chamber to a pressure of not higher than 1 mTorr. The particle dislodging cycle is repeated at least once, and preferably repeated at least twice so that a total of three particle dislodging cycles are carried out.

The number of particles that have fallen onto a top surface of the substrate is then counted by a counting apparatus, such as a KLA particle counter. The step of evacuating the process gas from the chamber can be carried out by a factory vacuum source.

In the particle dislodging cycle, at least one process gas selected from $Cl_2$, $BCl_3$ and Ar can be flown into the plasma chamber at a flow rate of at least 30 sccm, or to a chamber pressure of at least 6 mTorr, and preferably to a chamber pressure of at least 8 mTorr. The cycle of gas flowing/gas evacuation is repeated at least twice, and preferably repeated for at least three times in order to completely dislodge all contaminating particles and films from the interior surface of the chamber wall.

The present invention further discloses a method for detecting contaminating particles in a metal etch chamber that has polymeric or metal based particles or films adhered to an interior chamber wall which can be carried out by the various steps of first providing an etch chamber that is equipped with an etch gas inlet and a plasma source, conducting a metal etching process of a substrate in the etch chamber thus generating polymeric or metal based contaminating particles adhered to an interior chamber wall, evacuating the etch chamber to a pressure of not higher than 1 mTorr, conducting a particle dislodging cycle in the etch chamber by a two-step process of first flowing at least one etch gas into the chamber at a flow rate of not less than 30 sccm, and then evacuating the at least one etch gas from the chamber to a pressure of not higher than 1 mTorr, then repeating the particle dislodging cycle at least once, and detecting the contaminating particles present on a top surface of the substrate.

An illustration of the present invention novel method for dislodging contaminating particles from the interior chamber wall surface is shown in FIG. 3, by the dashed line. It is seen that a chamber pressure of about 8 mTorr of a process gas of either $Cl_2$, $BCl_3$ or Ar is reached in five separate particle dislodging cycles. Each cycle is carried out in a time period of about 20 seconds. It should be noted that while five separate cycles were shown in FIG. 3, the present invention novel method can be satisfactorily carried out in two or three cycles depending on the degree of contamination of the chamber wall. By utilizing the present invention novel method, the use of a lower chamber pressure is only necessary, i.e. at about 8 mTorr when compared to a chamber pressure of 12 mTorr or higher utilized in a conventional particle counting method, where only one cycle is utilized.

In the example shown in FIG. 3, the particle monitoring methodology is affected by creating a turbulent flow and gas pressure in a process chamber to monitor/detect chamber particle spike phenomenon. In the method, the recipe contains 4~6 repeated cycles of the following two steps: Step 1, throttle fully open (to vacuum)/no gas flow/20 sec; Step 2, throttle fully open (to vacuum)/80~120 sccm $Cl_2$/70~100 sccm $BCl_3$/30~50 sccm Ar/20 sec. The present invention novel method can be practiced after each PM (preventive maintenance) procedure, i.e. after about 4,000 wafers. The present invention novel method can also be practiced at each regular monitoring interval of about 500 wafers, or be practiced when the chamber alarm is triggered for backside heating problem indicating there are particles cumulated on the E-chuck (electrostatic chuck). The present invention novel method can be practiced by flowing a process gas from 0 mTorr to about 9 mTorr, or from 0 mTorr to about 12 mTorr in the etch chamber for effecting the removal or dislodging of particles from the interior chamber wall. The present invention novel method can be conveniently carried out by using production gases, i.e. the actual etching gases and the production flow rates of the gases. The best result, even though not always necessary, can be obtained when the processed gas is flown into the etch chamber to reach a chamber pressure of larger than 12 mTorr.

The desirable results obtained by using the present invention novel method in detecting particle contamination is shown in FIG. 4. A complete wafer lot of 24 wafers were tested after an etching process in an AEI (After Etching Inspection) test and in an ADI (After Developing Inspection) test. The particle counts after the AEI test is recorded in FIG. 4. It is seen that specifically wafer #19 has a serious contamination problem with a particle count of 74. The effectiveness of the present invention novel method has therefore been fully demonstrated.

The present invention novel method has been amply described in the above description and in the appended drawings of FIGS. 3 and 4.

While the present invention has been described in an illustrative manner, it should be understood that the terminology used is intended to be in a nature of words of description rather than of limitation.

Furthermore, while the present invention has been described in terms of a preferred embodiment, it is to be appreciated that those skilled in the art will readily apply these teachings to other possible variations of the inventions.

The embodiment of the invention in which an exclusive property or privilege is claimed are defined as follows.

What is claimed is:

1. A method for determining the number of contaminating particles in a process chamber comprising the steps of:
   providing a process chamber equipped with a gas inlet;
   conducting a chemical process on a substrate that generates contaminating particles in said chamber, evacuating a process gas from said chamber to a pressure of not higher than 1 mTorr;
   flowing at least one process gas used in said chemical process into said chamber at a flow rate of at least 30 sccm;
   evacuating said at least one process gas from said chamber to a pressure of not higher than 1 mTorr;
   flowing at least one process gas used in said chemical process into said chamber at a flow rate of at least 30 sccm;
   evacuating said at least one process gas from said chamber to a pressure of not higher than 1 mTorr; and
   counting number of particles that have fallen onto a top surface of said substrate.

2. A method for determining the number of contaminating particles in a process chamber according to claim 1, wherein said flowing/evacuating steps being repeated after a first cycle of flowing/evacuating steps at least two times.

3. A method for determining the number of contaminating particles in a process chamber according to claim 1, wherein said flowing/evacuating steps being repeated after a first cycle of flowing/evacuating steps at least three times.

4. A method for determining the number of contaminating particles in a process chamber according to claim 1 further comprising the step of evacuating said process gas from said chamber by a factory vacuum system.

5. A method for determining the number of contaminating particles. in a process chamber according to claim 1 further comprising the step of flowing said at least one process gas used in said chemical process into said chamber to reach a chamber pressure of at least 6 mTorr.

6. A method for determining the number of contaminating particles in a process chamber according to claim 1 further comprising the step of flowing said at least one process gas used in said chemical process into said chamber to a chamber pressure of at least 8 mTorr.

7. A method for determining the number of contaminating particles in a process chamber according to claim 1 further comprising the step of flowing said at least one process gas by flowing $Cl_2$ gas into said chamber to a chamber pressure of at least 8 mTorr.

8. A method for determining the number of contaminating particles in a process chamber according to claim 1 further comprising the step of flowing said at least one process gas by flowing $Cl_2$ gas into said chamber at a flow rate of at least 80 sccm.

9. A method for determining the number of contaminating particles in a process chamber according to claim 1 further comprising the step of flowing said at least one process gas by flowing $BCl_3$ gas into said chamber to a chamber pressure of at least 8 mTorr.

10. A method for determining the number of contaminating particles in a process chamber according to claim 1 further comprising the step of flowing said at least one process gas by flowing $BCl_3$ gas into said chamber at a flow rate of not less than 70 sccm.

11. A method for determining the number of contaminating particles in a process chamber according to claim 1 further comprising the step of flowing said at least one process gas by flowing Ar gas into said chamber to a chamber pressure of at least 8 mTorr.

12. A method for determining the number of contaminating particles in a process chamber according to claim 1 further comprising the step of flowing said at least one process gas by flowing Ar gas into said chamber at a flow rate of not less than 30 sccm.

13. A method for determining the number of contaminating particles in a process chamber according to claim 1 further comprising the step of flowing said at least one process gas by flowing $Cl_2$ at a flow rate not less than 80 sccm, $BCl_3$ at a flow rate not less than 70 sccm and Ar at a flow rate not less than 30 sccm into said chamber.

14. A method for determining the number of contaminating particles in a process chamber according to claim 1 further comprising the step of flowing said at least one process gas by flowing $Cl_2$, $BCl_3$ and Ar into said chamber to a chamber pressure of at least 8 mTorr.

15. A method for detecting contaminating particles in an etch chamber having polymeric or metal based particles adhered to an interior chamber wall comprising the steps of:
   providing an etch chamber equipped with a plasma source;
   conducting a metal etching process on a substrate in said etch chamber thus generating polymeric or metal based contaminating particles adhered to an interior chamber wall;
   evacuating said etch chamber to a pressure of not higher than 1 mTorr;
   conducting a particle dislodging cycle in said etch chamber comprising the steps of:

flowing at least one etch gas into said chamber at a flow rate of not less than 30 sccm;

evacuating said at least one etch gas from said chamber to a pressure of not higher than 1 mTorr;

repeating said particle dislodging cycle at least once; and detecting said contaminating particles present on a top surface of said substrate.

16. A method for detecting contaminating particles in an etch chamber according to claim 15 further comprising the step of detecting said contaminating particles present on the substrate by a particle counter.

17. A method for detecting contaminating particles in an etch chamber according to claim 15 further comprising the step of flowing at least one etch gas into said chamber selected from the group consisting of $Cl_2$, $BCl_3$ and Ar until a chamber pressure of 8 mTorr is reached.

18. A method for detecting contaminating particles in an etch chamber according to claim 15 further comprising the step of flowing at least one etch gas into said chamber at a flow rate between about 30 sccm and about 120 sccm.

19. A method for detecting contaminating particles in an etch chamber according to claim 15 further comprising the step of repeating said particle dislodging cycle at least twice.

20. A method for detecting contaminating particles in an etch chamber according to claim 15 further comprising the step of flowing $Cl_2$ at a flow rate not less than 80 sccm, $BCl_3$ at a flow rate not less than 70 sccm and Ar at a flow rate not less than 30 sccm into said chamber.

* * * * *